(12) United States Patent
Grant et al.

(10) Patent No.: US 9,456,792 B2
(45) Date of Patent: Oct. 4, 2016

(54) ADJUSTABLE HEAD POSITIONING DEVICE FOR USE WITH CONE BEAM CT SCANNER

(71) Applicants: Gerald T. Grant, Kensington, MD (US); Shayne A. Kondor, Powder Springs, GA (US)

(72) Inventors: Gerald T. Grant, Kensington, MD (US); Shayne A. Kondor, Powder Springs, GA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 21 days.

(21) Appl. No.: 14/303,368

(22) Filed: Jun. 12, 2014

(65) Prior Publication Data

US 2015/0359493 A1    Dec. 17, 2015

(51) Int. Cl.
| | |
|---|---|
| *H05G 1/00* | (2006.01) |
| *A61B 6/04* | (2006.01) |
| *A61B 6/14* | (2006.01) |
| *A61B 6/03* | (2006.01) |
| *A61B 6/00* | (2006.01) |

(52) U.S. Cl.
CPC .............. *A61B 6/04* (2013.01); *A61B 6/035* (2013.01); *A61B 6/0407* (2013.01); *A61B 6/14* (2013.01); *A61B 6/4085* (2013.01)

(58) Field of Classification Search
CPC .......... A61B 6/14; A61B 6/145; A61B 6/04; A61B 6/032
USPC ....................... 378/38–40, 62, 208
See application file for complete search history.

(56) References Cited

U.S. PATENT DOCUMENTS

| | | | |
|---|---|---|---|
| 5,947,981 A * | 9/1999 | Cosman ............... | A61B 6/0421 128/869 |
| 2010/0021862 A1 * | 1/2010 | Mah ..................... | G03B 42/042 433/140 |
| 2012/0244490 A1 * | 9/2012 | Tamburrino ......... | A61C 19/045 433/73 |

* cited by examiner

*Primary Examiner* — Courtney Thomas
(74) *Attorney, Agent, or Firm* — Ning Yang; Albert M. Churilla; Diane P. Tso (57) ABSTRACT

A heading positioning apparatus and the method of use for cone-beam computed tomography (CBCT), and single photon emission computed tomography (SPECT).

9 Claims, 6 Drawing Sheets

ADJUSTABLE HEAD POSITIONING DEVICE FOR USE WITH CONE BEAM CT SCANNER

CROSS-REFERENCE TO RELATED APPLICATIONS

This application claims the benefit of U.S. Provisional Application No. 61/834,192, filed 12 Jun. 2013.

BACKGROUND

Cone-beam computed tomography (CBCT) are widely employed and have many applications. In the past decade, they have become increasingly popular in the dental industry in many diagnostic and treatment procedures, such as dental implants, temporomandibular joint, orthodontics, impaction, orthognathic surgery, caries diagnosis, endodontics and the detection of periapical pathosis.

Dental cone beam computed tomography, also called cone beam volumetric tomography (CBVT), uses a single sweep of a conical x-ray beam around the patient's head to acquire a volume of anatomical data, e.g. a patient's jaws or part thereof. Similar to single or multi-slice CT scanner, the x-ray sensors or detectors in CBCT scanners are positioned opposite of the x-ray source to collect a map of x-ray absorption through the head of the patient. The central axis of the patient's anatomical volume of interest determines the locations of the x-ray source and sensor. The axis of rotation of source and sensor needs to correspond to the central axis of the volume of data.

Image data from CBCT is produced by reconstruction software, which creates a data set for a given volume that is called the field of view (FOV). Typically the quality of the image data is at its best towards the center of the FOV. Contemporary CBCT scanners are available with a variety of FOVs ranging from small, e.g. 4 cm diameter by 4 cm height, to large, e.g. 17 cm diameter by 23 cm height.

In standard usage the patient is aligned in the scanner, which may require the patient to stand, sit or lie to position their head between source and sensor. The position of the patient in the scanner is then adjusted so that the desired structures lie within the boundaries of a selected field of view. This is achieved by moving the patient's head in the FOV or moving the FOV over the patient's region of interest.

The FOV and the patient's region of interest are typically aligned with the aid of e.g. laser alignment beam projecting an illuminated line onto the patient's face. Where only laser beams are used to align the patient there are usually provided two or three intersecting laser "lines" which represent the visible projection of a 2d projection of a plane onto the patient's face, which typically run in X Y and Z alignment. Typically the central axis or the center of the volume is defined by the intersection of these lines, but alternative alignments may be sometimes required, depending upon the precise alignment and set-up of the system. The FOV and patient's position may be confirmed or improved with "scout" view exposures. The "scout" views are lateral or anterior-posterior plain x-ray projections on to the sensor that allow the operator to check that the region of interest actually lies within the boundaries of the chosen FOV.

Because CBCT's radiation dose is typically higher than that of conventional radiography, it is important to consider its diagnostic efficacy for each procedure to reduce radiation exposure. Radiation exposure to the patient may be reduced by reducing the size of the FOV. However, in real practices, it is much easier to acquire high quality images for a particular Region of Interest (ROI) using a larger FOV, which clearly results in increased radiation exposure. The difficulty associated with imaging a small ROI within a small FOV may be overcome if it is possible to easily center the FOV over the central axis of the ROI and thus reducing these doses by judicious adjustment of exposure factors and limiting the field of view to the smallest dimensions consistent with the clinical situation.

In recent years, many researchers have tried to expand the CBCT's use into facial and cranial reconstruction surgeries. Traditionally, reconstruction of head and facial injuries, are based only on post-traumatic 3-dimensional CT scans captured after the traumatic event, necessitates multiple operating room visits. These are required due to non-existent pre-injury images which would greatly assist in the fabrication of craniofacial implants to replace the missing structures. As a result implants must be custom fabricated, fitted and adjusted which is both time consuming and labor intensive. Additionally, due to the absence of any pre-injury information, the prolongation of treatment can lead to a less than optimum esthetic outcome. CBCT's ability to generate both hard and soft tissue images using a fraction of the radiation at a lower cost place it at an advantage over conventional CT scans and other three dimensional photogrammetric systems that capture the entire head.

These attributes also make CBCT ideal for use in military populations to establish pre-existing images of these tissues for deploying personnel. In the event of a traumatic injury, the patient's digital data can be retrieved. When used in conjunction with post-traumatic injury images, the information will permit the reconstructive team to formulate a complex treatment plan, fabricate custom guides and custom craniofacial implants prior to the first surgery.

However, CBCT also has several drawbacks which may adversely affect its efficiency and efficacy for craniofacial applications. Having accurate and reliable measurements of hard and soft tissues are especially important in facial/cranial reconstruction, such as the tissue thickness for specific landmarks of the face and scalp. CBCT acquisition typically requires about 60 seconds with a full gantry rotation, which covers about 15 breathing cycles. Thus, single breath-hold CBCT is impractical. Therefore, when organs move during respiration, CBCT can only generate a blurred composite organ volume rather than a true organ volume. Although some 4-D CBCT image acquisition techniques are being investigated, they either require long imaging time (such as segmented breath-hold acquisitions), deliver poor image quality (e.g., re-binning of projection data from a gated image acquisition), or excessive dose (e.g., respiratory re-sorting technique).

Another drawback of CBCT is the requirement of full rotational clearance of the gantry with respect to the position of the patient and couch. This is potentially problematic for alignment devices requiring substantial immobilization and patient support. Although smaller rotation angles (180 degrees plus a fan angle) may be reasonable for CBCT reconstruction, it still requires clearance of 360 degrees for gantry rotation. Yet another drawback of CBCT is its relatively high radiation dose, which can range from 2 to 9 cGy for optimal image quality. Repeat imaging will result in higher cumulative doses.

These limitations of CBCT are not due to CBCT itself, but are principally due to the mechanical limitations of patient alignment and localization. Thus there is a great need for a better patient positioning device, which allows easy alignment and localization of the patient while improving image quality and reducing patient's radiation exposure.

Existing and previous methods to position a human subject's head in a CBCT device include chin cups, oral bite tabs, head straps, and face nets (see U.S. Pat. No. 5,947,981, WO 2010089639, EP2278923 and US Pub No. 20010228907). These head positioning devices are normally supplied by the manufacturer of the CBCT device, and are generally specific to the device. These existing devices typically do not allow for fine adjustment of head position of the subject. They also fail to help the subject maintain a constant facial expression during and immediately after the CBCT scanning session, which could reduce image artifacts.

An example of the existing head positioning device are the three positioning attachments provided with the Kodak K9000/9300/9500 CBCT for use with the built in temple positioning guides, which include: a chin cup, an elastic head strap and a universal bite tab. The chin cup helps to quickly positions the subject. However, it impinges on, and deforms the chin. The elastic head strap helps to attach the device on patient's head but is incapable to fix the position of jaw or the gap between the teeth. The universal bite tab does not effectively resist movements of the head nor allow fine positing adjustment. As a result the CBCT scan images are often degraded by motion artifacts because of minor head moves. Important anatomy can be missed if positioning is not maintained. Furthermore, none of these existing devices fix nor maintain the facial expression of the subject.

This invention provides a head positioning device for properly aligning and localizing a patient's head and facial expression for procedures using a diagnostic imaging system, such as a cone-beam computed tomography (CBCT), or a single photon emission computed tomography (SPECT). However, it will be appreciated that the described technique may also find application in other imaging systems, other medical scenarios, or other medical techniques.

DETAILED DESCRIPTION OF THE INVENTION

Definitions

Vertical position of the head: The position of the head in a direction in line with the body, related to raising or lowering the head within the Cone Beam CT apparatus Longitudinal position of the head: the Anterior-posterior positioning of the head, related to the movement forward and backward Medial/lateral movement: movement of the head toward the center or away from the center of the normal head positions, related to the turning of the head toward or away from the center of the bite position.

Figure 1:
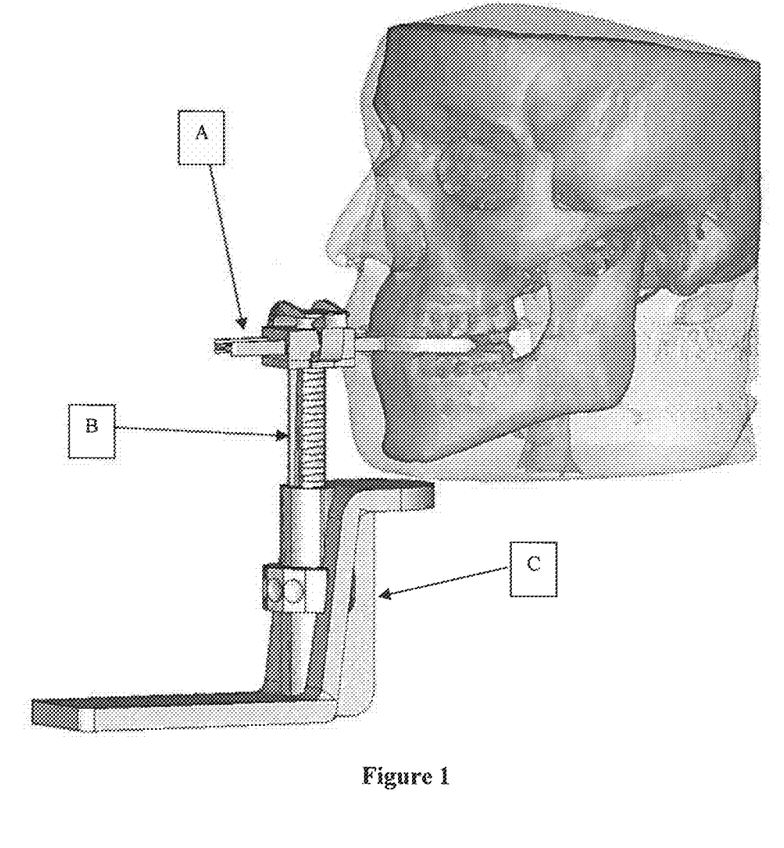
FIG. 1 an illustration of a CBCT Head Positioning unit.
Figure 2:
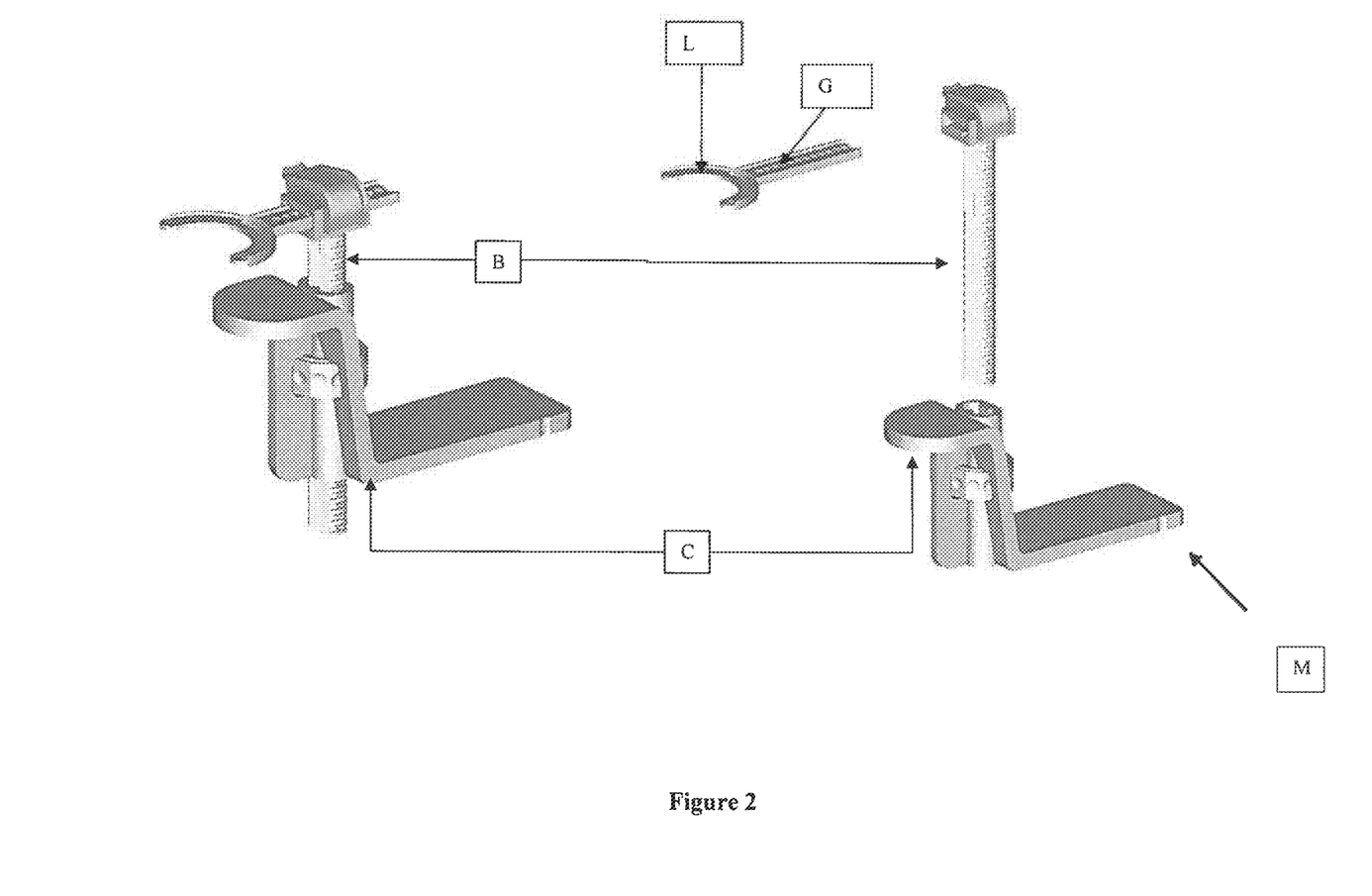
FIG. 2 CBCT Head Positioning Device Shown in Isometric and Exploded Views: (A) Biteplate; (B) Vertical Post with Adjustable Height; (C) Base Adapter to CBCT Scanner by groves on either sides (M).
Figure 3:
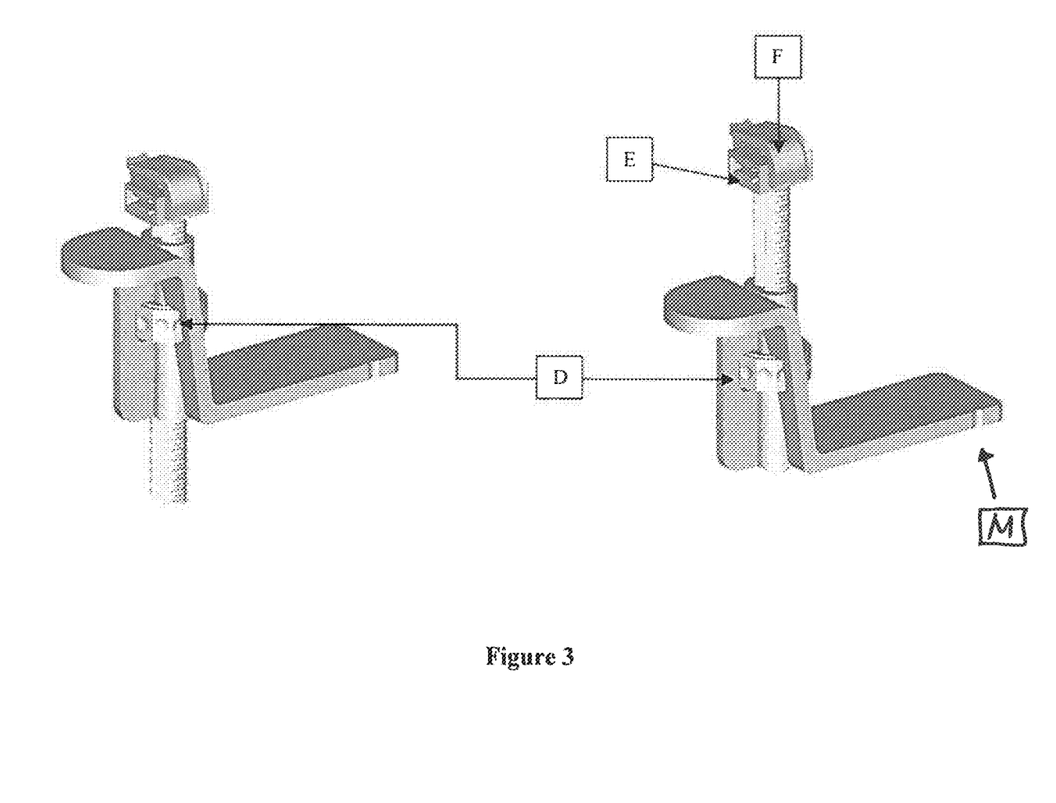
FIG. 3 Detail view of Vertical Post Height Adjustment Using Thumbwheel (D)

An illustration of an embodiment of the head positioning device of this invention is shown in FIG. 1, with isometric and exploded views shown in FIG. 2. An inventive head positioning device comprises a biteplate attachment (A), an adjustable vertical positioning post (B) adapted to engage and hold the biteplate attachment and a base adapter (C) that is adapted to engage and hold the vertical post, and can be attached to a CBCT machine. The head positioning of this invention is an improvement over the existing head positioning apparatuses because the use of a biteplate, which prevents the deformation of soft tissue of the face due to the use of a chin cup or strap during scanning, particularly around the jaw. The bite plate also allows a separation of upper and lower teeth by a predefined vertical distance of the thickness of the biteplate. The inventive device allows small precise vertical and longitudinal (anterior/posterior) adjustment of the head position by moving the vertical positioning post up and down through the base adapter using a thumbwheel (D) and screws (B) on the base adapter. It also helps the subject to maintain a fixed facial expression immediately before and after the CBCT scan for photograph or 3-D scan.

The head positioning device of this invention is intended to align and localize the position of a human subject's head in a Cone Beam CT (CBCT) scanner, relative to the scanner's field of view, without impinging on the soft tissue of the face and neck, while helping the subject to maintain a constant facial expression (FIG. 1). The inventive head positioning device also provides a means to adjust the vertical and longitudinal (anterior/posterior) positions of the subject's head relative to the CBCT scanner's field of view, while restricting medial/lateral movements, and any rotations of the head. Restricted head motion ensures high quality scan images and reduces motion artifacts, so that the intended anatomy appears within the field of view clearly. Lastly, the biteplate attachment provides a means to maintain constant distance between the teeth, and assist in fixing the subject's facial expression. Fixed facial expression is necessary for registration of post-CBCT photographs, or three dimensional scans, with the volume captured by the CBCT scanner in order to make an accurate registration of the two images. Changes in facial expression between the CBCT and three dimensional surfaces reconstructed from photographs will adversely affect the accuracy of image registration. The photographs need to be precisely registered to soft tissue boundaries within the reconstructed CBCT data.

The biteplate attachment (A) is a removable component of the inventive device, providing a mechanical interface with the subject, and fixture of the subject's head position. An embodiment of a biteplate attachment comprises a dental biteplate (L), and a position tab (G) projecting outward from the middle of the dental plate (see FIG. 2). The dental plate (L) is adapted for insertion into the mouth of a subject (see FIG. 1). Dental biteplate designs may be varied in shape and size to accommodate different mouth dimensions, arch-forms, and malocclusions. Type indicators may be engraved in a conspicuous location on the biteplate (e.g. "M" for medium, FIG. 4).

Thickness of the dental plate sets a precise gap between the subject's upper and lower teeth, which may be in the range of approximately 0.2-5 mm and preferably in the range of approximately 1-3 mm. The position tab (G) is adapted to be inserted into a keyslot located on the top end of the adjustable vertical position post, and may move freely within the keyway or locked down to at a desired position. In one embodiment, the positioning tab (G) has notches in equal interval, which allowing precious readings of the distance between the dental biteplate and the vertical positioning post. The notches are also part of the locking mechanism allowing it to be locked to the vertical positioning post. While engaged in the vertical post, stiffness of the biteplate tab needs to resist head motions. The cross-section of the tab is designed to maximize bending stiffness and minimize motion when engaged in the keyed slot (F) on the vertical position post (C). The oral biteplate may be made of any radiolucent, sanitary (USP Class I-VI) polymer material possessing sufficient elastic modulus to provide necessary structural stiffness, adequate yield strength to insure head position is maintained under normal forces, and low enough friction coefficient (in interface with the linear bearing surface and thumbwheel treads) to provide smooth insertion into the key slot. An example of such material is ABS polymer. The position tab and the dental biteplate may be made of different or the same material, but are both intended to be disposable.

Figure 5:
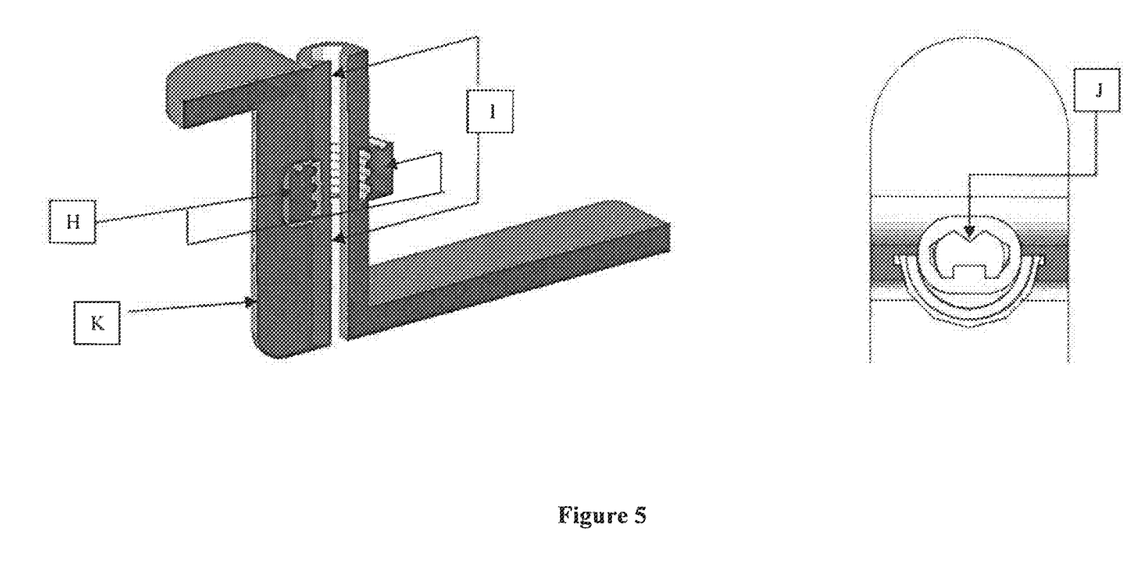
FIG. 5 Top view (j) of the of Linear Bearing Shaft (H) and Thumbwheel Thread (I) in Crossection and Linear Bearing Keyway FIG. 6 Example of Properly Positioned Subject

The vertical positioning post (B) features a specially designed cross-section intended to maximize bending and torsional stiffness, while minimizing linear bearing. A cross-section shape (J) is shown in FIG. 5. Helical thread may be cut into the medial and lateral surfaces of the vertical positioning post (B). This thread is matched to the internal thread (I) of the captive thumbwheel (D), which is engaged on the thread notches of the vertical positioning post (B). A linear bearing journal (H), which is integral to the base adapter, holds the vertical post with a single degree of freedom. Mechanical tolerances between the vertical post, linear bearing surface, and thumbwheel internal threads are set to provide smooth vertical post height adjustment with minimal slip, hysteresis, or torsional play. The vertical positioning post may be fabricated from the same radiolucent ABS material as the biteplate attachment or other materials such as resin, photopolymers, injection molded plastics or other materials with the same physical characteristics. Some examples include polycarbonate, nylon, PTFE, PEEK, PEKK, fiber-reinforced composite, or ceramics.

Figure 6:
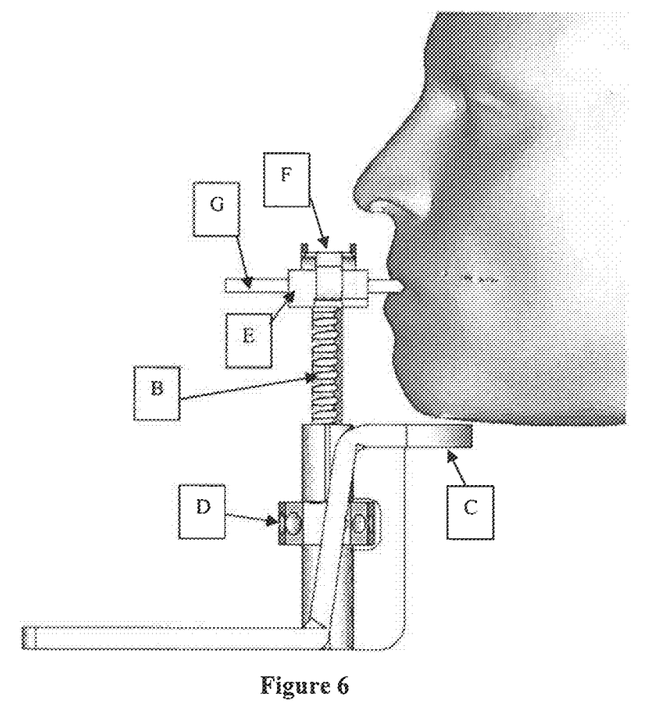

The base adapter (C) is adapted directly from the specifications of an original positioning device supplied by the different CBCT scanners. A base adapter normally comprises a chin rest affixing a patient's head position vertically. The major improvements to the base adapter include: integration of the special cross-section (J), linear bearing journal (H), the height adjustment thumbwheel (D), and incorporation of a gusset (K) to improve structural stiffness. FIG. 6 shows head positioning using a device of the present invention and a base adapter for the Kodak K9500 CBCT scanner. The subject's chin is slightly above the base adapter, insuring that the inferior mandible to be within the CBCT's field of view. The vertical post and base adapter can be fabricated using any material with similar radiolucency, elastic modulus, yield strength and friction coefficient as ABS. Base and vertical post specifications can be varied to adapt to other CBCT scanners.

Figure 4:
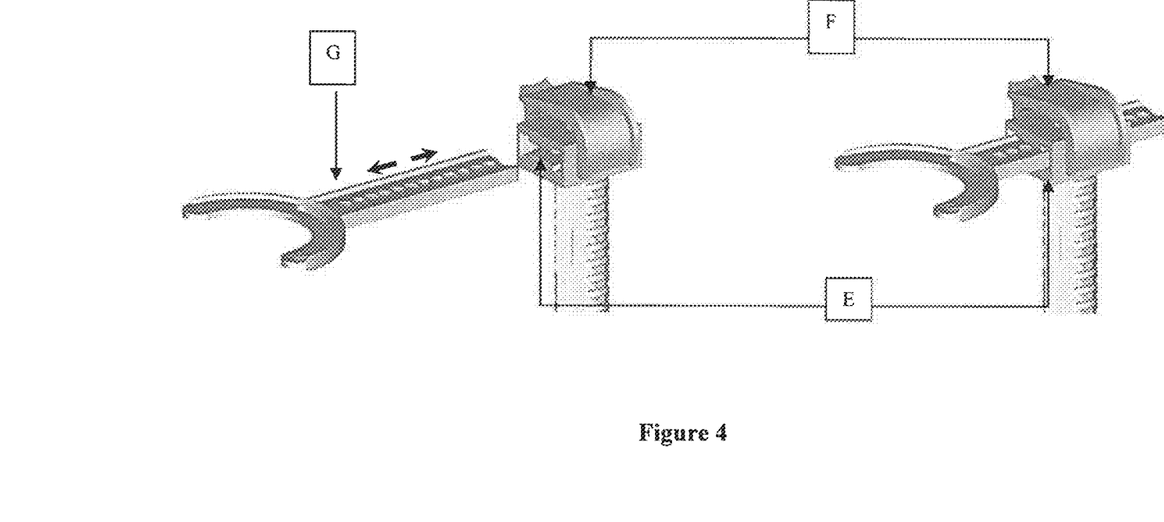
FIG. 4 Detail view of Biteplate Insertion into Keyed Hole on Vertical Post $\epsilon$ and Engagement of Sprung Pin (F) into Notches on the BitePlate Tab (G)

In an exemplary use of the inventive device, a subject first places the dental biteplate (L) of a biteplate attachment (A) in the mouth, and is then asked to clench his/her teeth onto the dental biteplate (L) as illustrated in FIG. 1. The positioning tab (G) of the biteplate attachment (A) is then locked into the vertical positioning post (B) as illustrated in FIG. 4 to ensure correct alignment in the scanner's field of view. In one embodiment, the positioning tab (G) extending from the dental biteplate is inserted into a key slot (F) located on the top of the vertical positioning post (B). To engage the biteplate attachment into the vertical positioning post, a CBCT operator pulls back spring tab (E) within the key slot (F) with a thumb and forefinger, allowing the positioning tab to slide freely though the key slot (F). Once the subject's head is in the desired longitudinal (anterior/posterior) position, the spring tab (E) is released, allowing a pin to engage the notches on the biteplate (G), and locking the dental biteplate in position. Longitudinal position can be locked to any one of the discrete positions of the notches on the biteplate tab (G). The vertical position of the biteplate may be adjusted by raising or lowering the vertical positioning post as shown in FIG. 4. In one embodiment, the CBCT operator turns a thumbwheel (D) to move the vertical post to a desired height, and lock it in position. FIG. 5 shows the details of the vertical post (B) interface with the base adapter (C) when a subject is correctly positioned using the inventive device. A linear bearing journal (H), integral to the base adapter, holds the vertical post with a single degree of freedom. Threads on the sides of the vertical post (B) engage the internal thread (I) of a captive thumbwheel (D). Rotation of the thumbwheel (D) slides the vertical post along its only degree of freedom (up and down), while friction in the threads hold the desired position. The CBCT operator can gauge precise height adjustment by the number of turns of the thumbwheel multiplied by the pitch of the thread. When the CBCT scan is completed, the biteplate is released from the vertical adjustment post by lifting the spring tap with a thumb and fore finger, backing out the position tab of the biteplate attachment out of the key slot (F) as the subject continues to clench the biteplate in their teeth. While the subject retains the biteplate in this manner, the same facial expression is maintained, and captured for post-CBCT photographs. Using a variety of available cameras and techniques, a set of photographs can be reconstructed into an accurate three dimensional surface containing additional information not captured in the CBCT scan, ion particular skin color, eye color, and hair color cranial anatomy outside of the CBCT field of view (FOV).

REFERENCES

1. Nizam A, Gopal L, Hakim A, Samsudin A: dimensional Accuracy of the Skull Models produced by Rapid Prototyping Technology Using Steriolithography Appartatus. Arch Oro Sciences 2006; 1:60-66
2. Galantucci L M, et al.: Reverse engineering techniques applied to a human skull for CAD 3D reconstruction and physical replication by rapid prototyping. J Med Eng Tech, Vol 30, No 2, March/April 2006; 102-111
3. Furultan M, Fallahi B, Mottavalli S, Dujouvy M: Steriolithography: Application in neurosurgery. Crit Rev Neurosurg (1998); 203-208
4. Gronet P M, Waskewicz G A, Richardson: Preformed acrylic cranial implants using fused deposition modeling: a clinical report. J Prosthet Dent. 2003 November; 90(5): 429-433.
5. Mozzo P, Procacci C, Tacconi A, Tinazzi Martini P, Bergamo Andreis I A; A new volumetric CT machine for dental imaging based on cone-beam technique: preliminary results. Eur. Radiol. 8, 1558-1564 (1998)
6. van Steenberghe D, Ericsson I, Van Cleynenbreugel J, Schutyser F, Brajnovic I, Andersson M. High precisio planning for oral implants based on 3-D CT scanning. A new surgical technique for immediate and delayed loading. Appl Osseointegration Res 2004; 4: 27-31
7. Lee, S. Three-Dimensional Photography and It's Application to Facial Plastic Surgery. Arch Facial Plast surg/Vol 6, November/December 2004; 410-414.

8. Littlefield T, Kelly K, Cherney J, Beals S, Pomatto J. Development of a new three-dimensional cranial imaging system. J Craniofac Surg. 2004 January; 15(1): 175-81
9. Kau C, Cronin A, Durning P, Zhurov A, Sanham A, Richmond S. A new method for the 3D measurement of postoperative swelling following orthognathic surgery. Ortho and Craniofac Research. 2006 February; 9(1): 31-7.
10. Caloss R, Kevin Atkins K, Stella J. Three-Dimensional Imaging for Virtual Assessment and Treatment Simulation in Orthognathic Surgery. Oral and Maxillofacial Surgery Clinics of North America Vol 19(3), August 2007: 287-309

What is claimed is:

1. An adjustable head positioning apparatus for Cone Beam CT (CBCT) scanner, consisting:
   a. a biteplate attachment formed of a radiolucent material, comprising a dental biteplate and a positioning tab extending from the dental biteplate, wherein said dental biteplate is configured to fit within a patient's mouth, and mate with the patient's teeth;
   b. a vertical positioning post adapted to engage and lock the positioning tab of said biteplate attachment allowing longitudinal adjustment of the biteplate attachment, and
   c. a base adapter adapted to engage and lock the vertical positioning post, allowing vertical adjustments of the positioning post, wherein said base adapter is configured to be locked into a CBCT scanner.

2. The adjustable head positioning apparatus of claim 1, wherein thickness of a dental bite plate of said biteplate attachment separates the patient's upper and lower teeth at a precise distance.

3. The adjustable head positioning apparatus of claim 2, wherein said thickness is approximately 0.2-5 mm.

4. The adjustable head positioning apparatus according to claim 1, wherein said biteplate is configured to be detachably attached to an upper end portion of said vertical positioning post.

5. The adjustable head positioning apparatus according to claim 4, wherein said positioning post comprises a key slot defined in said upper end portion of the vertical positioning post and configured to receive said position tab of said biteplate attachment.

6. The adjustable head positioning apparatus according to claim 5, wherein said vertical positioning post allows longitudinal adjustment of the position of said dental biteplate and is configured to lock the said biteplate attachment in position.

7. The adjustable head positioning apparatus according to claim 1, wherein said vertical positioning post is configured to be detachably attached to said base adapter, which contains groves on the side to be locked into the CBCT scanner.

8. A method for positioning a subject's head for CBCT scanning without deformation of soft tissues of the face and neck,
   a. locking a base adapter to a CBCT machine;
   b. placing a biteplate attachment in a subject's mouth;
   c. asking the subject to clench his/her teeth onto a dental biteplate of said biteplate attachment;
   d. inserting a positioning tab of said biteplate attachment into an adjustable vertical positioning post;
   e. adjusting the subject's head to desired longitudinal position relative to the scanner's field of view;
   f. locking the biteplate attachment onto an adjustable vertical positioning post;
   g. adjusting vertical head position by moving vertical post to a desired height; and
   h. locking vertical post in position to base adapter.

9. A method for post-CBCT photographs or three dimensional scans after an CBCT scan using head positioning apparatus of claim 1,
   a. releasing biteplate from the adjustable vertical positioning post as a subject continues to clench the biteplate in the teeth; and
   b. capturing photographs or three dimensional scan images using the same CBCT scanner while the subject retains the biteplate.

* * * * *